United States Patent
Lin et al.

(10) Patent No.: US 11,344,587 B2
(45) Date of Patent: May 31, 2022

(54) METHOD OF IMPROVING UROGENITAL HEALTH USING PROBIOTIC BACTERIA

(71) Applicant: TCI CO., LTD., Taipei (TW)

(72) Inventors: Yung-Hsiang Lin, Taipei (TW);
Chu-Han Huang, Taipei (TW);
Cheng-Yu Ho, Taipei (TW)

(73) Assignee: TCI CO., LTD., Taipei (TW)

( * ) Notice: Subject to any disclaimer, the term of this patent is extended or adjusted under 35 U.S.C. 154(b) by 145 days.

(21) Appl. No.: 16/692,265

(22) Filed: Nov. 22, 2019

(65) Prior Publication Data

US 2020/0338145 A1 Oct. 29, 2020

(30) Foreign Application Priority Data

Apr. 26, 2019 (TW) .................................. 108114789

(51) Int. Cl.
*A61K 35/747* (2015.01)
*A61P 31/10* (2006.01)
*A61P 31/04* (2006.01)
*A61P 13/02* (2006.01)

(52) U.S. Cl.
CPC ............ *A61K 35/747* (2013.01); *A61P 13/02* (2018.01); *A61P 31/04* (2018.01); *A61P 31/10* (2018.01)

(58) Field of Classification Search
None
See application file for complete search history.

(56) References Cited

U.S. PATENT DOCUMENTS

2008/0131462 A1* 6/2008 Graf ..................... A61K 35/747
424/246.1

FOREIGN PATENT DOCUMENTS

CN 102802648 A 11/2012
CN 102839136 A 12/2012

OTHER PUBLICATIONS

Ruiz et al. Curr. Microbio. (2009) 59, 497-501 (Year: 2009).*
Atassi et al. FEMS Microbiol Lett 304 (2010) 29-38 (Year: 2010).*
Examination report dated Oct. 30, 2020, listed in correspondent Taiwan patent application No. 108114789 (publication No. TW202038980).
Examination report dated Oct. 11, 2021 listed in correspondent Chinese patent application No. 201911058410.0 (publication No. CN111849799).

* cited by examiner

*Primary Examiner* — Jana A Hines
*Assistant Examiner* — Khatol S Shahnan Shah
(74) *Attorney, Agent, or Firm* — Cheih-Mei Wang

(57) ABSTRACT

Provided is a method of improving urogenital health, including administering to a subject a composition including an effective amount of a *Lactobacillus johnsonii* strain deposited under the accession number of DSM 33288 or a metabolite thereof. The *Lactobacillus johnsonii* strain, which is a probiotic, and metabolites thereof inhibit the growth of common pathogenic bacteria and fungi causing genitourinary tract infections, thereby reducing the risk of genitourinary tract infections or alleviating symptoms thereof. Also provided is a composition for improving urogenital health which includes the *Lactobacillus johnsonii* strain.

7 Claims, 4 Drawing Sheets

Specification includes a Sequence Listing.

Mock control

*Lactobacillus johnsonii* DSM 33288

Mock control

*Lactobacillus johnsonii* DSM 33288

METHOD OF IMPROVING UROGENITAL HEALTH USING PROBIOTIC BACTERIA

CROSS-REFERENCE TO RELATED APPLICATION

This application claims priority of Taiwan patent application No. 108114789, filed on Apr. 26, 2019, the content of which is incorporated herein in its entirety by reference.

BACKGROUND OF THE INVENTION

1. Field of the Invention

The present invention relates to a method for health care by using a probiotic bacterial strain. Particularly, the present invention relates to a method of improving urogenital health by using a novel *Lactobacillus johnsonii* strain.

2. The Prior Art

Previous studies have shown that the rectum, vagina, and bladder in females are in close proximity anatomically so that microorganisms in the gut can enter the genitourinary tract via bacterial adhesion. This process is considered natural that provides the vagina and outer urethra with the microflora required to maintain health condition. Under normal circumstances, various Lactobacilli such as *Lactobacillus crispatus* and *Lactobacillus jenesenii*, colonize the vagina and form the dominant populations, which exclude pathogens from the vagina, produce lactic acid and maintain a pH value of 3.8 to 4.5 in the vagina to inhibit the propagation of pathogens, and produce antibacterial substances and hydrogen peroxide to kill other microorganisms.

When the vagina and outer urethra are deficient in normal flora due to various reasons, such as estrogen deficiency, antibiotic treatment, and use of spermicide during sexual intercourse, the risk of urogenital infection often increases. Moreover, because females, compared with males, have shorter urethra and smaller distance between the urethra and the anus or the vaginal opening, they have a higher probability suffering from urinary tract infection via bacteria invasion from the vaginal opening or anus into the urethra. Common urogenital infections include bacterial vaginal infections, fungal vaginal infections, and urinary tract infections. The major pathogens for bacterial vaginal infections are anaerobic Gram-negative bacilli, such as *Gardnerella vaginalis*; fungal vaginal infections are mainly caused by *Candida albicans*; and urinary tract infections are usually caused by urinary pathogenic *Escherichia coli*. Although these infections can be treated by antibiotics, an increase in drug resistance of pathogens and the high recurrence of infections create new problems to be solved.

Current methods of preventing urogenital infections include ensuring a clean and dry genitourinary area, avoiding the use of irritating hygiene products, adequate water intake, and maintenance of immunity by lifestyle management and moderate exercise. However, for modern people having heavy school workloads or being busy at work, there are difficulties in keeping a regular lifestyle. Therefore, it is of necessity to develop novel strategies that help to maintain urogenital health in a convenient manner.

SUMMARY OF THE INVENTION

Accordingly, the present invention provides a method of improving urogenital health, including administering to a subject a composition including an effective amount of a *Lactobacillus johnsonii* strain or a metabolite thereof, wherein the *Lactobacillus johnsonii* strain is deposited with Deutsche Sammlung von Mikroorganismen and Zellkulturn GmbH (DSMZ; Inhoffenstr. 7B, D-38124 Braunschweig, Germany) under the accession number of DSM 33288. The strain is also deposited with Bioresource Collection and Research Center (BCRC; 331, Shih-Pin Rd., Hsinchu 30062, Taiwan) under the accession number of BCRC 910885.

In another aspect, the present invention provides a composition for improving urogenital health, including an effective amount of the abovementioned *Lactobacillus johnsonii* strain or a metabolite thereof, and a pharmaceutically acceptable carrier.

In one embodiment of the invention, the *Lactobacillus johnsonii* strain or the metabolite thereof inhibits growth of a bacterial or fungal pathogen causing a urinary tract infection. The bacterial or fungal pathogen causing the urinary tract infection includes Gram-negative bacteria such as *Escherichia coli* and *Staphylococcus* spp.

In one embodiment of the invention, the *Lactobacillus johnsonii* strain or the metabolite thereof inhibits growth of a bacterial pathogen causing a bacterial vaginal infection. The bacterial pathogen causing the bacterial vaginal infection includes *Gardnerella vaginalis, Streptococcus* spp., and *Staphylococcus* spp.

In one embodiment of the invention, the *Lactobacillus johnsonii* strain or the metabolite thereof inhibits growth of a fungal pathogen causing a fungal vaginal infection. The fungal pathogen causing the fungal vaginal infection includes *Candida* spp., such as *Candida albicans*.

The *Lactobacillus johnsonii* strain described herein and metabolites thereof can inhibit the growth of various bacteria and fungi causing urogenital infections, and thus can be utilized to prepare a urogenital healthcare composition for reducing the risk of genitourinary tract infections or alleviating symptoms thereof. The composition may be in the form of a powder, a granule, a liquid, or a paste, and may be manufactured as a medicament, food, a drink, or a nutritional supplement that may be administered to a subject orally or topically.

In view of previous studies showing that microorganisms in the human gut can enter the genitourinary tract via bacterial adhesion, it is evident to those skilled in the art that supplement of appropriate amounts of the *Lactobacillus johnsonii* strain DSM 33288 can expand the population of this probiotic in the intestine, which increases the possibility of more of the probiotic entering the genitourinary tract and ultimately leads to improved urogenital health.

The present invention is further explained in the following examples, in reference to the accompanying drawings. It should be understood that the examples given below do not limit the scope of the invention, and that modifications can be made without departing from the scope of the appended claims.

DETAILED DESCRIPTION OF THE PREFERRED EMBODIMENT

Figure 1A:
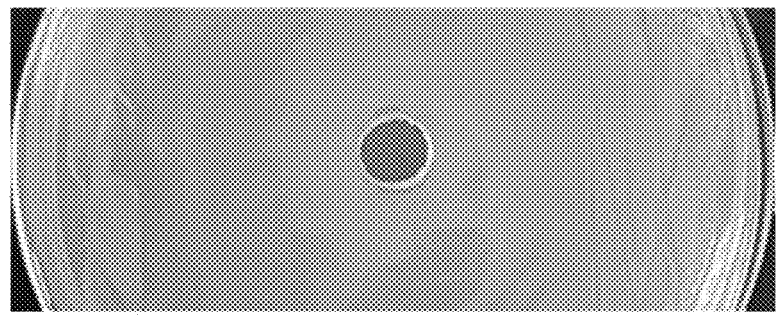
FIG. 1A and FIG. 1B are photographs respectively showing the growth of an *Escherichia coli* strain untreated (mock control) or treated with a culture supernatant of the *Lactobacillus johnsonii* strain according to one embodiment of the invention.

The present invention provides a method of improving urogenital health by using a *Lactobacillus johnsonii* strain, which is isolated from human breast milk and is identified as a novel strain after culture and strain identification. The strain has been deposited with DSMZ under the accession number of DSM 33288. The following examples show that the *Lactobacillus johnsonii* strain and metabolites thereof can significantly inhibit the growth of a variety of bacteria and fungi causing genitourinary tract infections, and show that the *Lactobacillus johnsonii* strain is resistant to gastric acid and bile salts.

Definition

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The expression "an effective amount" as used herein refers to the amount of an active ingredient required to elicit a particular effect in a subject. As appreciated by those skilled in the art, the effective amount will vary depending on the route of administration, the use of excipients, and the possible co-administration with other substances.

The procedures and conditions for bacterial culture described herein are within the professional competence and routine techniques of those skilled in the art.

The term "metabolite(s)" as used herein refers to any substance that is produced during bacterial metabolism and secreted into a bacterial culture when the bacteria culture is prepared.

The expression "pharmaceutically acceptable carrier" includes one or more agents selected from the group consisting of solvents, emulsifiers, suspending agents, decomposers, binding agents, excipients, stabilizing agents, chelating agents, diluents, gelling agents, preservatives, lubricants, absorption delaying agents, liposomes, and the like. The selection and amount for use of these agents are based on conventional techniques within the profession of those skilled in the art.

The aforementioned pharmaceutically acceptable carrier includes a solvent selected from the group consisting of water, normal saline, phosphate buffered saline (PBS), a sugar-containing solution, and combinations thereof.

Materials and Methods
Bacterial and Fungal Strains

The bacteria or fungi used in the following examples include the *Lactobacillus johnsonii* strain DSM 33288, which was isolated from human breast milk and identified by sequence alignment of 16S rRNA genes (the 16S rRNA gene of the strain disclosed herein has the nucleotide sequence of SEQ ID NO: 1); a *Gardnerella vaginalis* strain (BCRC 17040; also deposited under ATCC 14018) purchased from BCRC; an *Escherichia coli* strain isolated from human feces, and a *Candida* strain isolated from the stems of *Brassica juncea*.

Culturing of *Lactobacillus Johnsonii*

The *Lactobacillus johnsonii* strain DSM 33288 was seeded at 1% in Lactobacilli MRS medium (BD Difco Lactobacilli MRS Broth; Thermo Fischer Scientific) and cultured statically at 37° C. for about 16 hours. The resulting bacterial culture (approximately $5 \times 10^9$ CFUs/mL) was centrifuged at 5000 rpm for 20 minutes, and the culture supernatant was collected for subsequent analysis. The culture supernatant contains the metabolites of the *Lactobacillus johnsonii* strain.

Example 1

Inhibition of the Growth of Bacterial Pathogens Causing Urinary Tract Infections by Using the *Lactobacillus Johnsonii* Strain In order to assess the inhibitory effect of the *Lactobacillus johnsonii* strain disclosed herein on urinary tract infection pathogens, an *Escherichia coli* strain isolated from human feces was used as an exemplary pathogen in the growth inhibition assay. Briefly, the *E. coli* strain was seeded at 1% in LB medium (BD Difco LB Broth, Miller; Thermo Fischer Scientific) and cultured at 37° C. for about 16 hours with agitation at 150 rpm, followed by applying 100 µL of the *E. coli* culture (approximately $5 \times 10^8$ CFUs/mL) on an LB agar plate (LB medium containing 1.5% agar) with a central depression. Thereafter, 50 µL of the culture supernatant of the *Lactobacillus johnsonii* strain disclosed herein was added to the depression of the LB agar plate covered with the *E. coli* (experimental group). For comparison, a mock control was prepared similarly but without treatment with the culture supernatant of the *Lactobacillus johnsonii* strain. The two LB agar plates were cultured statically at 37° C. for 24 hours for examination of the presence of zone of inhibition.

Figure 1B:
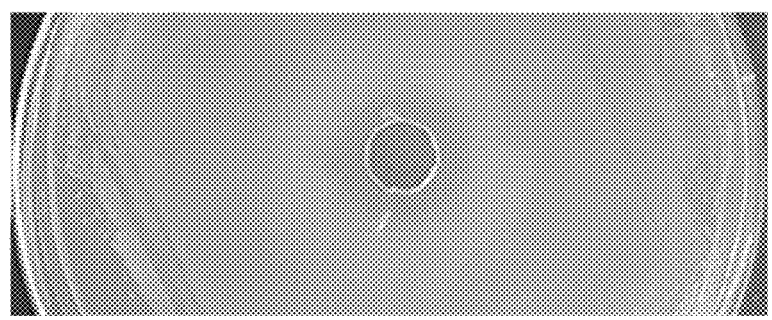

FIG. 1A and FIG. 1B are photographs showing the LB agar plates in the mock control and the experimental group, respectively, after the 24-hour culture. According to FIG. 1A and FIG. 1B, a vast amount of *E. coli* grew around the plate depression in the blank control, whereas in the experimental group, a circular zone of inhibition with a diameter of about 1.3 cm (with an inner diameter of about 0.6 cm) was observed around the plate depression. The results indicate that the *Lactobacillus johnsonii* strain DSM 33288 and metabolites thereof can effectively inhibit the growth of bacterial pathogens causing urinary tract infections.

Example 2

Inhibition of the Growth of Bacterial Pathogens Causing Bacterial Vaginal Infections by Using the *Lactobacillus Johnsonii* Strain In order to assess the inhibitory effect of the *Lactobacillus johnsonii* strain disclosed herein on bacterial vaginal infection pathogens, a *Gardnerella vaginalis* strain ATCC 14018

(also deposited under BCRC 17040) was used as an exemplary pathogen in the growth inhibition assay. Briefly, the *G. vaginalis* strain was seeded at 1% in LB medium (BD Difco LB Broth, Miller; Thermo Fischer Scientific) supplemented with 5% sheep blood and cultured statically at 37° C. for about 16 hours, followed by applying 100 μL of the *G. vaginalis* culture (approximately $1 \times 10^8$ CFUs/mL) on a blood agar plate (BD BBL Trypticase™ Soy Agar medium (Thermo Fischer Scientific) containing 5% sheep blood) with a central depression. Thereafter, 50 μL of the culture supernatant of the *Lactobacillus johnsonii* strain disclosed herein was added to the depression of the blood agar plate covered with the *G. vaginalis* (experimental group). For comparison, a mock control was prepared similarly but without treatment with the culture supernatant of the *Lactobacillus johnsonii* strain. The two blood agar plates were cultured statically at 37° C. for 24 hours for examination of the presence of zone of inhibition.

Figure 2A:
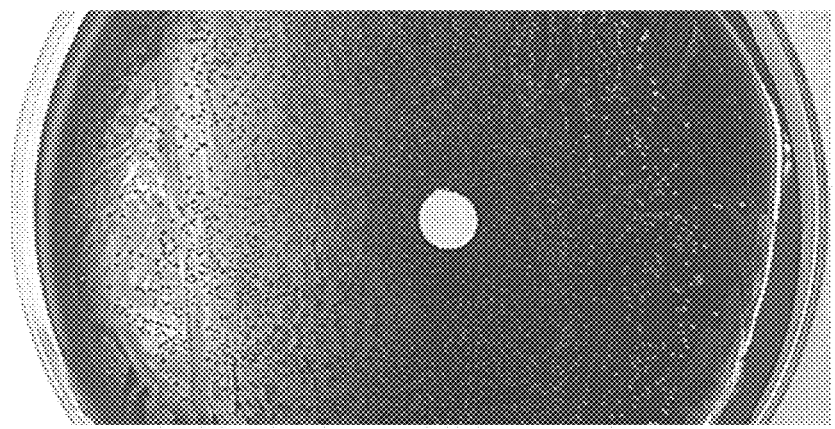
FIG. 2 and FIG. 2B are photographs respectively showing the growth of a *Gardnerella vaginalis* strain untreated (mock control) or treated with a culture supernatant of the *Lactobacillus johnsonii* strain according to one embodiment of the invention.
Figure 2B:
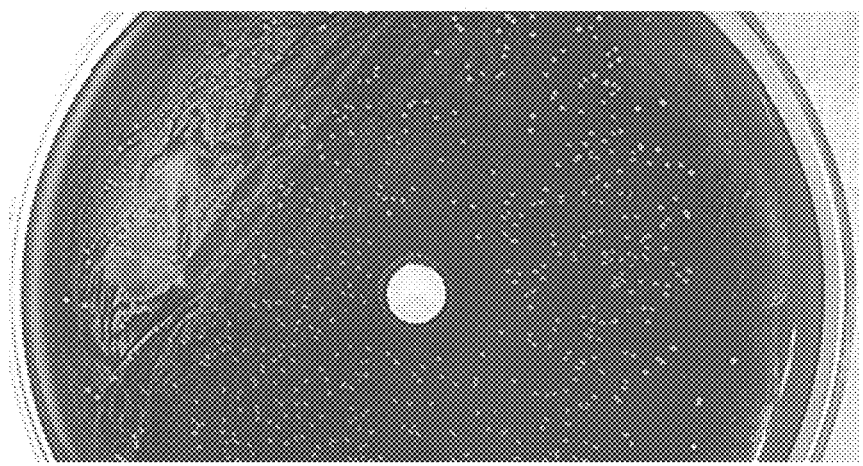

FIG. 2A and FIG. 2B are photographs showing the blood agar plates in the mock control and the experimental group, respectively, after the 24-hour culture. According to FIG. 2A and FIG. 2B, the *G. vaginalis* grew around the plate depression in the blank control, whereas in the experimental group, a circular zone of inhibition with a diameter of about 1.6 cm (with an inner diameter of about 0.6 cm) was observed around the plate depression. The results indicate that the *Lactobacillus johnsonii* strain DSM 33288 and metabolites thereof can effectively inhibit the growth of bacterial pathogens causing bacterial vaginal infections.

Example 3

Inhibition of the Growth of Fungal Pathogens Causing Fungal Vaginal Infections by Using the *Lactobacillus Johnsonii* Strain In order to assess the inhibitory effect of the *Lactobacillus johnsonii* strain disclosed herein on fungal vaginal infection pathogens, a *Candida* yeast strain isolated from the stems of *Brassica juncea* was used as an exemplary pathogen in the growth inhibition assay. Briefly, the *Candida* yeast strain was seeded at 1% in yeast extract-peptone-dextrose (YPD) medium (BD Difco YPD Broth; Thermo Fischer Scientific) and cultured statically at 30° C. for about 16 hours, followed by applying 100 μL of the *Candida* yeast culture (approximately $2 \times 10^7$ CFUs/mL) on a YPD agar plate (YPD medium containing 1.5% agar) with a central depression. Thereafter, 50 μL of the culture supernatant of the *Lactobacillus johnsonii* strain disclosed herein was added to the depression of the YPD agar plate covered with the *Candida* yeast (experimental group). For comparison, a mock control was prepared similarly but without treatment with the culture supernatant of the *Lactobacillus johnsonii* strain. The two YPD agar plates were cultured statically at 37° C. for 24 hours for examination of the presence of zone of inhibition.

Figure 3A:
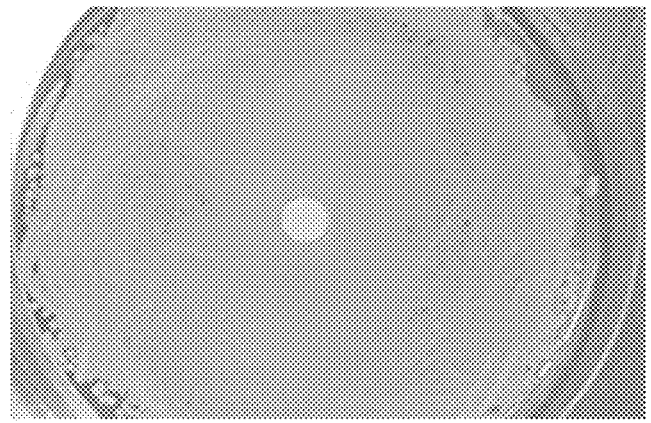
FIG. 3A and FIG. 3B are photographs respectively showing the growth of a *Candida* strain untreated (mock control) or treated with a culture supernatant of the *Lactobacillus johnsonii* strain according to one embodiment of the invention.
Figure 3B:
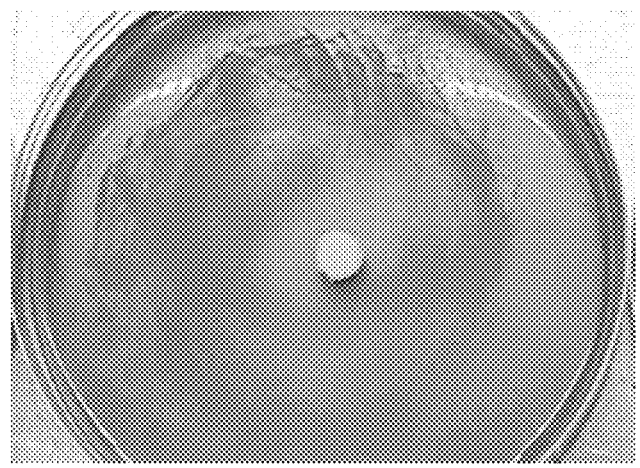

FIG. 3A and FIG. 3B are photographs showing the YPD agar plates in the mock control and the experimental group, respectively, after the 24-hour culture. According to FIG. 3A and FIG. 3B, the *Candida* yeast covered the plate around the depression in the blank control, whereas in the experimental group, a circular zone of inhibition with a diameter of about 2.3 cm (with an inner diameter of about 0.6 cm) was observed around the plate depression. The results indicate that the *Lactobacillus johnsonii* strain DSM 33288 and metabolites thereof can effectively inhibit the growth of fungal pathogens causing fungal vaginal infections.

Example 4

The Acid Resistance and Bile Salt Resistance of the *Lactobacillus Johnsonii* Strain In order to verify whether the *Lactobacillus johnsonii* strain disclosed herein survives the acidic environment of the stomach and tolerates the bile salts in the intestine, an overnight liquid culture of the *Lactobacillus johnsonii* strain (approximately $5 \times 10^9$ CFUs/mL) was subjected to gastrointestinal simulation tests using artificial gastric juice or artificial intestinal fluid. In the gastric simulation test, the artificial gastric juice (a 0.2% sodium chloride aqueous solution with a pH of 1.2, 2, or 3), to which was added 1% by volume of the bacterial culture, was incubated at 37° C. for 3 hours with agitation at 50 rpm. In the intestinal simulation test, the artificial intestinal fluid (an aqueous solution containing 0.68% potassium dihydrogen phosphate and 0.1%, 0.2%, or 0.3% oxgall, pH 6.8), to which was added 1% by volume of the bacterial culture, was incubated at 37° C. for 3 hours with agitation at 50 rpm. For comparison, a bile-salt-free aqueous solution at pH 7 containing 0.2% sodium chloride or 0.68% potassium dihydrogen phosphate and incubated with the overnight culture of the *Lactobacillus johnsonii* was used as a control. Thereafter, 100 μL of the bacterial solution obtained from each test was applied to a Lactobacilli MRS agar plate and cultured overnight at 37° C. for bacterial counting.

Figure 4:
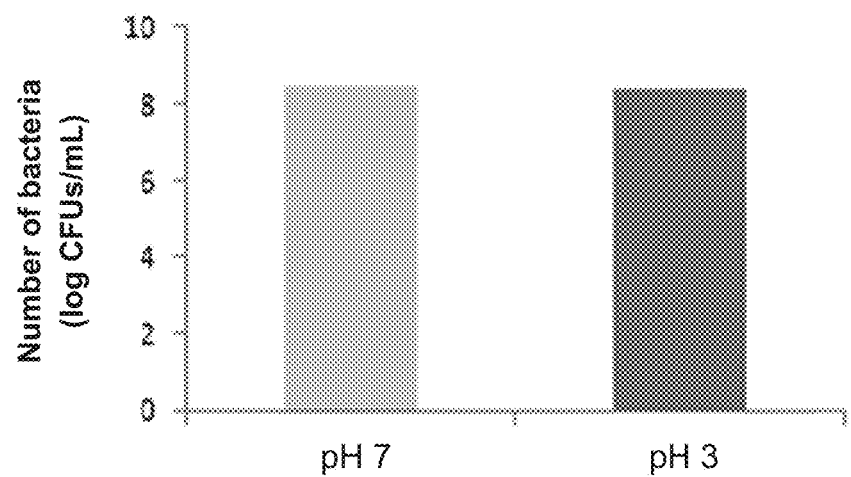
FIG. 4 shows change in the number of the *Lactobacillus johnsonii* disclosed herein in a gastric simulation test using artificial gastric juice.
Figure 5:
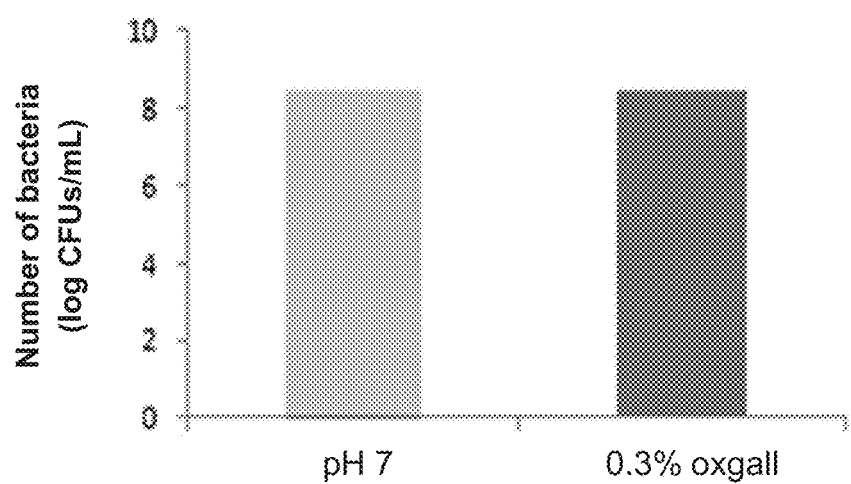
FIG. 5 shows change in the number of the *Lactobacillus johnsonii* disclosed herein in an intestinal simulation test using artificial intestinal fluid.

According to FIG. 4, the number of the *Lactobacillus johnsonii* incubated for 3 hours in the artificial gastric juice (pH 3) was almost the same as that of the *Lactobacillus johnsonii* incubated at pH 7, indicating that the *Lactobacillus johnsonii* strain is resistant to gastric acid. According to FIG. 5, the number of the *Lactobacillus johnsonii* incubated for 3 hours in the artificial intestinal fluid (containing 0.3% oxgall) was almost the same as that of the *Lactobacillus johnsonii* incubated in the absence of bile salts, indicating that the *Lactobacillus johnsonii* strain is tolerant to bile salts. These results indicate that the *Lactobacillus johnsonii* strain DSM 33288 survives in the digestive tract after entering the human body via oral administration. Therefore, this strain can exert the inhibitory effect on the growth of pathogenic bacteria or fungi in the genitourinary tract.

In conclusion, the *Lactobacillus johnsonii* strain described herein and metabolites thereof can inhibit the growth of common pathogenic bacteria and fungi causing urogenital infections, and thus can be utilized to prepare a urogenital healthcare composition. The composition may be in the form of a powder, a granule, a liquid, or a paste, and may be manufactured as a medicament, food, a drink, or a nutritional supplement that may be administered to a subject orally or topically.

The present invention has been described with reference to the above preferred embodiments. However, it will be apparent to those skilled in the art that modifications and changes in form and detail may be made without departing from the scope of the present invention defined by the appended claims.

What is claimed is:

1. A method of improving urogenital health, comprising orally administering to a subject a composition comprising an effective amount of a *Lactobacillus johnsonii* strain, wherein the *Lactobacillus johnsonii* strain is deposited under the accession number of DSM 33288.

2. The method of claim 1, wherein the *Lactobacillus johnsonii* strain inhibits growth of a bacterial or fungal pathogen causing a urinary tract infection.

3. The method of claim 2, wherein the bacterial or fungal pathogen causing the urinary tract infection is *Escherichia coli*.

4. The method of claim 1, wherein the *Lactobacillus johnsonii* strain growth of a bacterial pathogen causing a bacterial vaginal infection.

5. The method of claim 4, wherein the bacterial pathogen causing the bacterial vaginal infection is *Gardnerella vaginalis*.

6. The method of claim 1, wherein the *Lactobacillus johnsonii* strain inhibits growth of a fungal pathogen causing a fungal vaginal infection.

7. The method of claim 6, wherein the fungal pathogen causing the fungal vaginal infection is *Candida* spp.

* * * * *

SEQUENCE LISTING

<160> NUMBER OF SEQ ID NOS: 1

<210> SEQ ID NO 1
<211> LENGTH: 1094
<212> TYPE: DNA
<213> ORGANISM: Lactobacillus johnsonii

<400> SEQUENCE: 1

```
caatctgtct atattagacg gctgactcct ataaaggtta tcccaccggc tttgggtgtt      60
acagactctc atggtgtgac gggcggtgtg tacaaggccc gggaacgtat tcaccgcggc     120
gtgctgatcc gcgattacta gcgattccag cttcgtgtag gcgagttgca gcctacagtc     180
cgaactgaga acggctttca gagatccgct tgccttcgca ggttcgcttc tcgttgtacc     240
gtccattgta gcacgtgtgt agcccaggtc ataagggggca tgatgacttg acgtcatccc     300
caccttcctc cggtttgtca ccggcagtct cattagagtg cccaacttaa tgatggcaac     360
taatgacaag ggttgcgctc gttgcgggac ttaacccaac atctcacgac acgagctgac     420
gacagccatg caccacctgt ctcagcgtcc ccgaagggaa ctcctaatct cttaggtttg     480
cactggatgt caagacctgg taaggttctt cgcgttgctt cgaattaaac cacatgctcc     540
accgcttgtg cgggcccccg tcaattcctt tgagtttcaa ccttgcggtc gtactcccca     600
ggcggagtgc ttaatgcgtt agctgcagca ctgagaggcg gaaacctccc aacacttagc     660
actcatcgtt tacggcatgg actaccaggg tatctaatcc tgttcgctac ccatgctttc     720
gagcctcagc gtcagttgca gaccagagag ccgccttcgc cactggtgtt cttccatata     780
tctacgcatt ccaccgctac acatggagtt ccactctcct cttctgcact caagttcaac     840
agtttctgat gcaattctcc ggttgagccg aaggctttca catcagactt attgaaccgc     900
ctgcactcgc tttacgccca ataaatccgg acaacgcttg ccacctacgt attaccgcgg     960
ctgctggcac gtagtagcgt gactttctag tatacgtcaa taagcagtac tactctatct    1020
tcctcactac acagagctta cgagcggaaa ccctcctccc tcacgcggcg tgctcatcag    1080
acttgcgtcc atgt                                                      1094
```